United States Patent [19]

Kubota et al.

[11] Patent Number: 4,862,000
[45] Date of Patent: Aug. 29, 1989

[54] METHOD FOR PREDICTING DENSITY OF MICRO CRYSTAL DEFECTS IN SEMICONDUCTOR ELEMENT FROM SILICON WAFER USED IN THE MANUFACTURE OF THE ELEMENT, AND INFRARED ABSORPTION MEASUREMENT APPARATUS FOR THIS METHOD

[75] Inventors: Atsuko Kubota, Yokohama; Yoshiaki Matsushita, Kawasaki; Yoshiaki Ohwada, Yokohama, all of Japan

[73] Assignee: Kabushiki Kaisha Toshiba, Kawasaki, Japan

[21] Appl. No.: 15,039

[22] Filed: Feb. 17, 1987

[30] Foreign Application Priority Data

Feb. 25, 1986 [JP] Japan .................................. 61-38265

[51] Int. Cl.$^4$ .............................................. G01J 3/42
[52] U.S. Cl. ..................................... 250/341; 250/339
[58] Field of Search ...................... 250/339, 338.4, 341, 250/358.1

[56] References Cited

U.S. PATENT DOCUMENTS

| | | | |
|---|---|---|---|
| 3,868,185 | 2/1975 | Genzel et al. | 250/339 |
| 4,429,047 | 1/1984 | Jastrzebski et al. | 436/4 |
| 4,590,574 | 5/1986 | Edmonds et al. | 250/339 |

FOREIGN PATENT DOCUMENTS 61-17031 1/1986 Japan .
1017031 1/1986 Japan .................................. 250/339

OTHER PUBLICATIONS

Cohen-Solal et al., "Epitaxial (CdHg) Te Infrared Photovoltaic Detectors" *Applied Physics Letters*, Nov. 15, 1971, vol. 19, No. 10, pp. 436–438.
Amerian National Standard, "Standard Test Method for Substitutional Atomic Carbon Content of Silicon by Infrared Absorption", pp. 523–524, F123-70T, Jan. 1976.
Kachmarsky et al., "Far-Infrared High Resolution Fourier Transform Spectrometer: Applications to $H_2O$, $NH_3$, and $NO_2$ Lines", *Applied Optics.*, vol. 15, Nov. 3, Mar. 1976, pp. 708–713.
Baluteau et al., "High Resolution Michelson Interferometer for Airborn Infrared Astronomical Observations", *Applied Optics*, No. 1–Concept and Performance, vol. 16, No. 7, Jul. 1977, pp. 1834–1840.
Langlet et al., "High Resolution Michelson Interferometer for Airborn Infrared Astronomical Observations, 2: System Design" *Applied Optics*, vol. 16, No. 7, Jul. 1977, pp. 1841–1848.
Agopian et al., "Determination of Interstitial Oxygen in Silicon using Internal Calibration with Two Phonon Peaks", IBM *Technical Disclosure Bulletin*, vol. 23, No. 4, Sep. 1980, pp. 1389–1390.
H. J. Humecki, "Infrared Spectroscopy and its Application to Contamination Analysis," Solid State Technology, vol. 28, No. 4, Apr., 1985, pp. 309–313.
D. A. Skoog, Principles of Instrumental Analysis, 3rd Edition, CBS College Publishing, 1985, pp. 124–128, 332–336.
D. G. Mead, "Applications of Infrared Spectroscopy to the Annealing of Silicon," Solid State Technology, vol. 24, No. 11, Nov., 1981, pp. 71–74.
A. Ohsawa et al., "Determination of Oxygen Concentration Profiles in Silicon Crystals Observed by Scanning IR Absorption using Semiconductor Laser," Applied Physics Letters, vol. 36, No. 2, Jan., 1980, pp. 147–148.
Shimura et al., "Heterogeneous Distribution of Interstitial Oxygen in Annealed Czochralski-Grown Silicon Crystals," Applied Physics Letters 38 (11), pp. 867–870, Jun. 1, 1981.

Primary Examiner—Janice A. Howell
Assistant Examiner—William F. Rauchholz
Attorney, Agent, or Firm—Finnegan, Henderson Farabow, Garrett, & Dunner

[57] ABSTRACT

In a method for predicting a density of micro crystal defects to be generated in a semiconductor element, an infrared absorption spectrum associated with a silicon wafer, which is used for the manufacture of the semiconductor element, is formed by a spectrum forming system. The spectrum has a first oxygen absorption peak at the wavenumber range of 1150 to 1050 cm$^{-1}$ and a second oxygen absorption peak at 530 to 500 cm$^{-1}$. First and second coefficients indicating oxygen concentrations at the first and second peaks are read by a reading unit. The density of the micro crystal defects are predicted by using a ratio of the first and second coefficients as a monitor.

5 Claims, 3 Drawing Sheets

METHOD FOR PREDICTING DENSITY OF MICRO CRYSTAL DEFECTS IN SEMICONDUCTOR ELEMENT FROM SILICON WAFER USED IN THE MANUFACTURE OF THE ELEMENT, AND INFRARED ABSORPTION MEASUREMENT APPARATUS FOR THIS METHOD

BACKGROUND OF THE INVENTION

The present invention relates to a method for predicting, by use of a silicon wafer, the density of micro crystal defects which may be produced when a silicon semiconductor element is formed from the silicon wafer, and an infrared absorption measurement apparatus used for embodying the method.

A substrate used in the manufacture of a silicon semiconductor element, i.e., a wafer, is normally prepared by the Czochralsky (CZ) method. A silicon wafer prepared by the CZ method contains about $10^{18}$ atoms/cm$^3$ of oxygen, and almost all oxygen atoms (about 95%) are located between lattices. These interstitial oxygen atoms are infrared active, and absorb incident infrared rays. An infrared absorption spectrum obtained by irradiating infrared rays on the wafer has a peak absorption coefficient of 30 cm$^{-1}$ and a half-value width of 36 cm$^{-1}$ at a frequency corresponding to wave-numbers of 1106 cm$^{-1}$ at room temperature. An absorption coefficient $\alpha 1106$ at this peak is proportional to the oxygen concentration of the wafer over a wide range.

Oxygen atoms contained in the silicon wafer in an oversaturation state are precipitated when the wafer is subjected to a thermal treatment during the manufacture of the semiconductor element, thus causing micro crystal defects. When these defects appear on an element-forming region of the wafer, the yield of the properly manufactured semiconductor elements is considerably reduced.

For this reason, conventionally, the oxygen concentration of wafers is specified in accordance with the manufacturing processes of semiconductor elements, and wafers having an oxygen concentration within a specified range are selected for the manufacture of semiconductor elements. Oxygen concentration [Oi] is calculated from the following equation and absorption coefficient $\alpha 1106$ measured as a monitor of an oxygen concentration by an infrared absorption method:

$$[Oi] = 3.01 \times 10^{17} \times \alpha 1106 \text{ atoms/cm}^3$$

However, when a plurality of wafers having the same oxygen concentration [Oi] are subjected to identical processes, the resulting micro crystal defect compositions cannot always be the same. For example, if a plurality of wafers, whose oxygen concentration is selected to fall within the range of 7 to $10 \times 10^{17}$ cm$^{-3}$, are subjected to an identical thermal treatment, a micro crystal defect density after the thermal treatment varies over the range of $10^7$ to $10^{10}$ cm$^{-3}$ for each wafer.

Micro crystal defects are greatly influenced by residual carbon in the wafer. Normal wafers prepared by the CZ method contain an amount ($< 2 \times 10^{16}$ cm$^{-3}$) of carbon which cannot be detected by the infrared absorption method. Nevertheless, the micro crystal defects cannot yet be controlled. For this reason, condition management during crystal growth and during manufacture, e.g., management of stability of a solid/liquid interface and thermal hysteresis, must be strictly performed. Therefore, the manufacture of semiconductor elements requires time and cost.

SUMMARY OF THE INVENTION

The present invention has been made in consideration of the above situation, and has as its object to provide a method which can predict, by use of a silicon wafer, the density of micro crystal defects produced when a semiconductor element is formed from the silicon wafer, before the manufacture of the semiconductor element, and an infrared absorption measurement apparatus for embodying the method.

The present inventors have found that an infrared absorption spectrum obtained by irradiating a silicon wafer with infrared rays had first and second oxygen absorption peaks and a ratio of oxygen concentrations obtained from these absorption peaks was closely related to the density of micro crystal defects produced during the manufacturing process of semiconductor elements. When the above ratio is used as a monitor, the density of micro crystal defects to be generated in a semiconductor element after the manufacturing process can be easily predicted by use of a wafer before the process.

The infrared absorption measurement apparatus of the present invention comprises spectrum forming means for forming an infrared absorption spectrum of a silicon wafer used in the manufacture of a semiconductor element; means for reading first and second coefficients indicating oxygen concentrations from first and second oxygen absorption peaks appearing in the spectrum; means for outputting a ratio of the first and second coefficients; and means for displaying the ratio.

DETAILED DESCRIPTION OF THE PREFERRED EMBODIMENTS

An embodiment of the present invention will now be described in detail with reference to the accompanying drawings.

Figure 1:
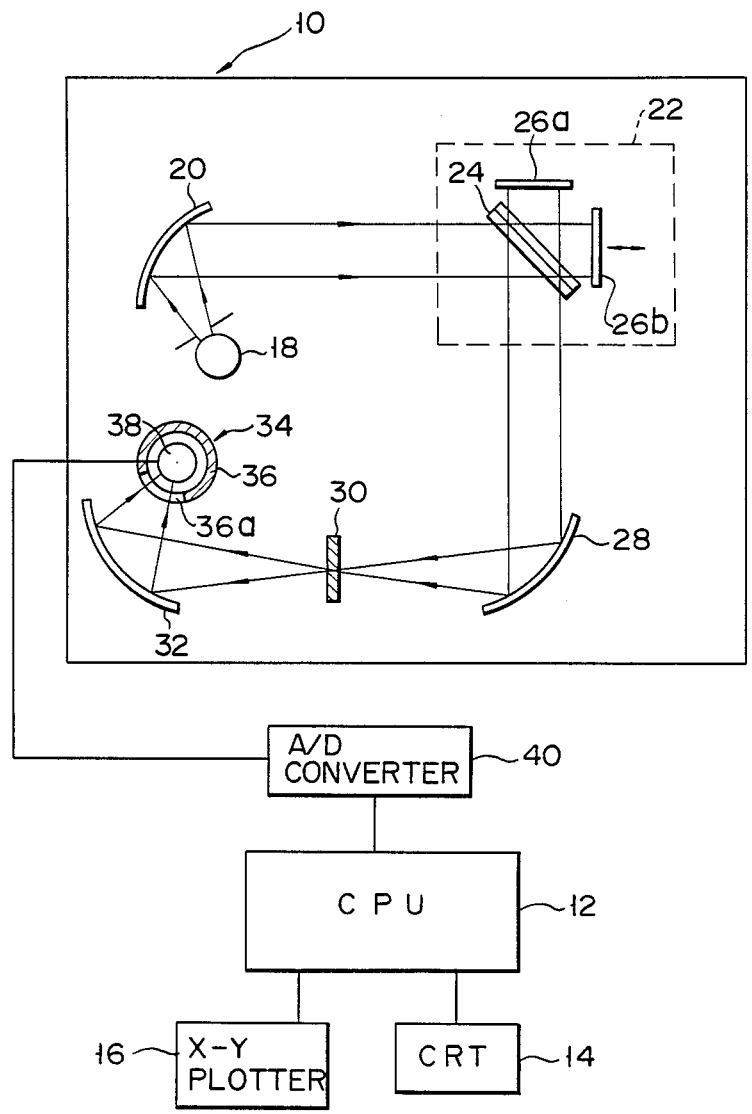
FIG. 1 is a schematic view showing a measurement apparatus according to a first embodiment of the present invention.

FIG. 1 shows a Fourier transform type infrared absorption measurement apparatus. This apparatus comprises optical system 10 for obtaining an interferogram, CPU 12 having an operational function, e.g., Fourier transform and a memory function for storing data, CRT 14 for displaying data, and X-Y plotter 16.

Optical system 10 has light source 18 for emitting infrared rays. Infrared rays emitted from light source 18 are reflected by reflection mirror 20 and converted to parallel beams, and are then incident on Michelson interferometer 22. Interferometer 22 has beam splitter 24, stationary mirror 26a, and movable mirror 26b. Interferometer 22 splits an incident light beam into two beams and, thereafter, allows them to interfere with each other. Interfered light beams (interferogram) from interferometer 22 are converged on test sample 30, i.e., a silicon wafer, by reflection mirror 28, and are partially absorbed by the sample. After passing through sample 30, the light beams are reflected by reflection mirror 32 to become incident on detector 34. The beam incident on detector 34 is photoelectrically converted thereby and is detected as an electrical signal. Detector 34 has cryostat 36 and photoconductive cell 38 which is housed in cryostat 36 together with liquid nitrogen. Cryostat 36 has window 36a for transmitting the interfered light beam from reflection mirror 32. Beam splitter 24 of interferometer 22 and window 36a of detector 34 are preferably formed of CsI (cesium iodide) which has a high transmittance for infrared rays and low noise within the wavenumber range of 530 to 500 cm$^{-1}$. $Hg_xCd_{1-x}Te$, having a high resolution within an available wavenumber range, is preferably used for photoconductive cell 38 of detector 34.

An interferogram detected by detector 34 is supplied to CPU 12 through A/D converter 40, and is stored therein. The interferograms are accumulated and averaged, and spectrum-Fourier-transformed by CPU 12. A spectrum of an infrared active impurity contained in test sample 30, i.e., an infrared absorption spectrum, is obtained by subtracting from the spectrum of the test sample an absorption spectrum of a standard sample which is specified in the ASTM, i.e., a pure standard sample which contains only impurities in the amount of a detection limit or lower by the infrared absorption method.

Figure 2:
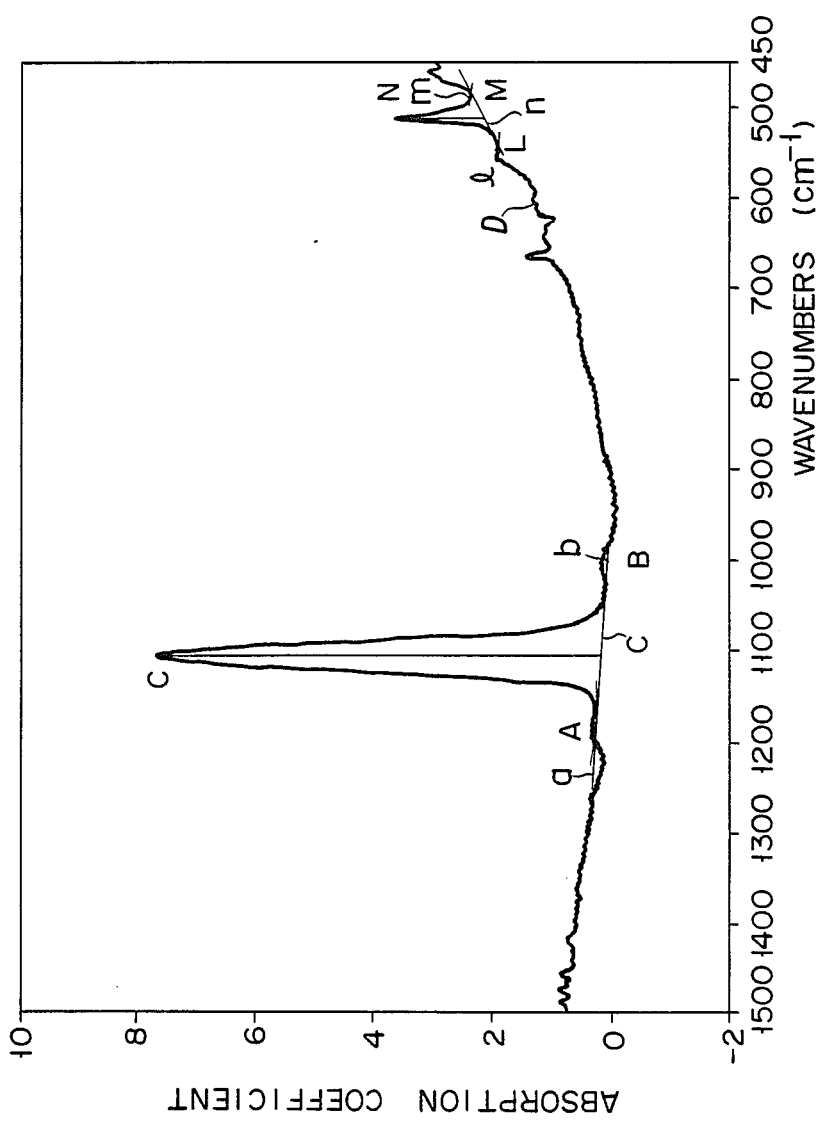
FIG. 2 is a view showing an infrared absorption spectrum obtained by the apparatus.

The obtained infrared absorption spectrum of test sample 30 is shown in FIG. 2. In this spectrum, peak C appearing at wavenumber 1106 cm$^{-1}$ is caused by interstitial oxygen atoms in sample 30, and peak N appearing at wavenumber 513 cm$^{-1}$ is caused by substitutional oxygen atoms. In addition, a peak appearing at wavenumber 607 cm$^{-1}$ is caused by carbon atoms in sample 30.

Absorption coefficient $\alpha Oi$ associated with an interstitial oxygen concentration, absorption coefficient $\alpha Os$ associated with a substitutional oxygen concentration, oxygen concentration [Oi] of sample 30, and ratio $\alpha Oi/\alpha Os$ of absorption coefficients are obtained by CPU 12 as follows:

(1) Average line a is drawn with respect to a spectrum within the wavenumber range of 1250 to 1150 cm$^{-1}$.

(2) Average line b is drawn with respect to a spectrum within the wavenumber range of 1040 to 980 cm$^{-1}$.

(3) Point A corresponding to wavenumber 1200 cm$^{-1}$ along line a and point B corresponding to wavenumber 1000 cm$^{-1}$ along line b are connected by a line, and the line is defined as base line c.

(4) A vertical height of interstitial oxygen peak point C present at wavenumber 1106 cm$^{-1}$ from base line c is read, and the height is obtained as absorption coefficient $\alpha Oi$.

(5) Oxygen concentration [Oi] of sample 30 is calculated from the following equation:

$$[Oi] = 3.01 \times 10^{17} \times \alpha Oi \text{ atoms/cm}^3$$

(6) Average line l is drawn with respect to a spectrum within the wavenumber range of 550 to 530 cm$^{-1}$.

(7) Average line m is drawn with respect to a spectrum within the wavenumber range of 500 to 480 cm$^{-1}$.

(8) Point L corresponding to wavenumber 540 cm$^{-1}$ on line l and point M corresponding to wavenumber 490 cm$^{-1}$ on line m are connected by a line, and the line is defined as base line n.

(9) A vertical height of substitutional oxygen peak point N present at wavenumber 513 cm$^{-1}$ from base line n is read, and the read height is obtained as absorption coefficient $\alpha Os$.

(10) Ratio $\alpha Oi/\alpha Os$ is calculated.

Subsequently, in the same manner as in procedures (1) and (4) above, absorption coefficient $\alpha Oc$ associated with carbon is obtained from an absorption peak appearing within the wavenumber range of 615 to 600 cm$^{-1}$.

Ratio $\alpha Oi/\alpha Os$ obtained as above is displayed on CRT 14 or is printed by a printer (not shown). Data [Oi], $\alpha Os$, and $\alpha Oc$ are also output by the printer, as needed. When oxygen concentration [Oi] and ratio $\alpha Oi/\alpha Os$ are measured by the apparatus, a measurement period can be three minutes for each measurement position.

The measurement results obtained by the measurement apparatus with the above arrangement are utilized in the manufacture of semiconductor elements as follows.

The present inventors measured an infrared absorption spectrum of 256-kb dynamic random-access memories prepared from various silicon wafers at a resolution of 4 cm$^{-1}$. A lot which was prepared from a silicon wafer with ratio $\alpha Oi/\alpha Os < 4.5$ ([Oi] = 7 to $10 \times 10^{17}$ cm$^{-3}$) provided an average product yield of 65%, and a lot prepared from a silicon wafer with ratio $\alpha Oi/\alpha Os > 4.5$ provided an yield of 45%.

In intrinsic gettering, in the conventional case of managing only oxygen concentration [Oi], a product yield varied over a range of 38% to 74% due to generation of micro crystal defects. However, when management was conducted using ratio $\alpha Oi/\alpha Os < 4.5$ as a monitor in addition to the conventional monitor, the product yield could be improved to 70%.

From these findings, it was found that a difference in ratio $\alpha Oi/\alpha Os$ appeared as a difference in yield. Therefore, ratio $\alpha Oi/\alpha Os$ obtained by the above apparatus is used as a new monitor in addition to oxygen concentration [Oi] of a wafer as the conventional monitor, so that the density of micro crystal defects which may be produced after the manufacture of a semiconductor element can be further accurately predicted. With the above measurement apparatus, a test sample can be easily measured without being cut or broken, and desirable wafers can be easily selected so as to improve a product yield.

In the normal CZ method, the ratio $\alpha Oi/\alpha Os$ of a wafer cut from an ingot cannot be decreased below 4.5. However, when an ingot pulled in a growth furnace by the CZ method is cooled, if a tail portion of the ingot is cooled over four hours at a temperature of 850° to 550° C. using a heater provided in the furnace, the ratio $\alpha Oi/\alpha Os$ of all the wafers cut from this ingot can be decreased below 4.5.

As described above, with the measurement apparatus of the present invention, ratio $\alpha Oi/\alpha Os$ of interstitial oxygen absorption coefficient and substitutional oxygen absorption coefficient in a silicon wafer can be easily measured. When the obtained ratio is used as a monitor for managing the manufacture of semiconductor elements together with an oxygen concentration which has been conventionally used, the density of micro crystal defects which may be produced in semiconductor elements manufactured from the silicon wafer can be accurately predicted from the state of wafer before the manufacture. Therefore, manufacturing management can be greatly simplified as compared to conventional methods, and product yield can be significantly improved.

The present invention is not limited to the above embodiment, and various changes and modifications may be made within the spirit and scope of the invention.

Figure 3:
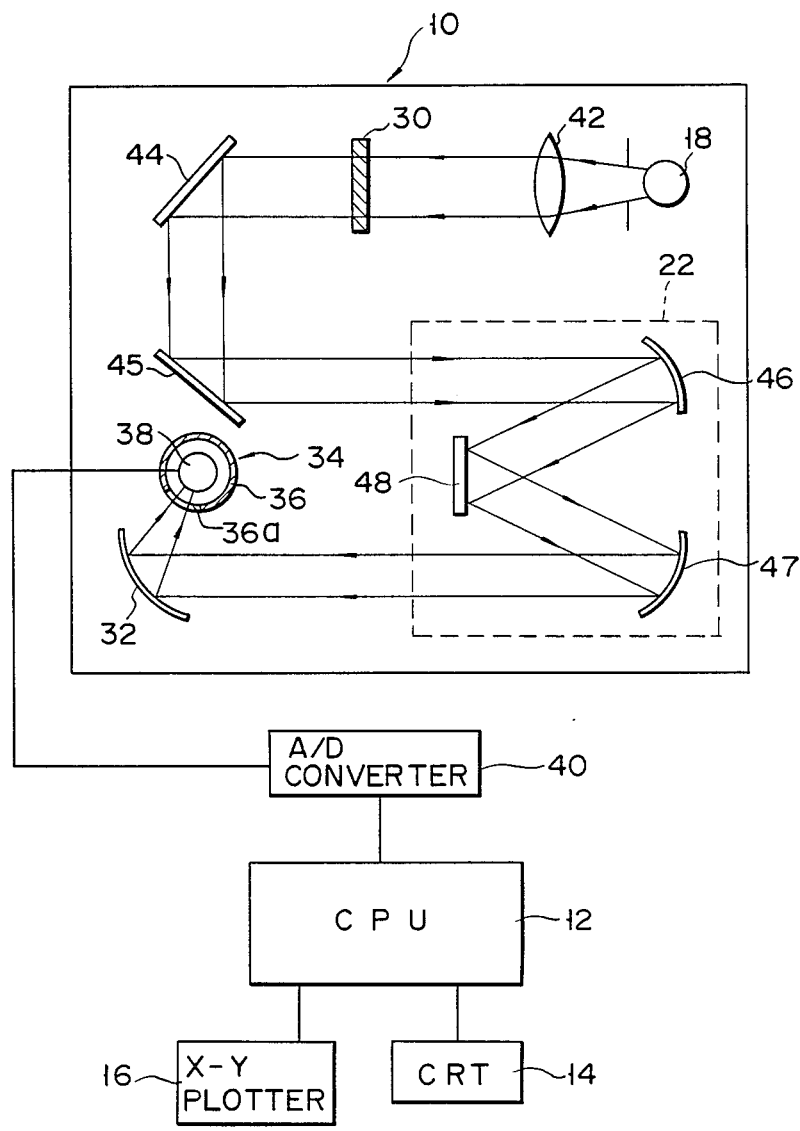
FIG. 3 is a schematic view showing a measurement apparatus according to a second embodiment of the present invention.

In the above embodiment, for example, as a means for splitting infrared rays emitted from a light source, a Michelson interferometer is used. However, the present invention is not limited to this. As shown in FIG. 3, dispersion type beam splitting unit 22 can be used. With this embodiment, infrared rays emitted from light source 18 are converted to parallel beams through collimator lens 42, and then become incident on test sample 30. The parallel beams are partially absorbed by sample 30, and are then reflected by reflection mirrors 44 and 45 to become incident on beam-splitting unit 22. Unit 22 has a pair of reflection mirrors 46 and 47 and diffraction grating 48. In this case, diffraction grating 48 has a blaze wavelength of 15 μm, and a resolution of about 0.5 $cm^{-1}$. The infrared rays incident on unit 22 are split into spectra by this unit. The beam is reflected by reflection mirror 32 and becomes incident on detector 34. Then, the beam is photoelectrically converted, and is detected as an electrical signal.

With the measurement apparatus with the above arrangement, ratio $\alpha Oi/\alpha Os$ of absorption coefficients of a test sample can be easily measured in the same manner as in the above embodiment.

An absorption coefficient is used as a coefficient indicating an oxygen concentration at an oxygen absorption peak appearing in an infrared absorption spectrum. However, any coefficient may be used as long as it can indicate the oxygen concentration.

In the above embodiment, the ratio of an interstitial oxygen concentration and an absorption coefficient is used as a monitor for micro crystal defects. A substitutional oxygen concentration or a carbon concentration can be used as a monitor together with the ratio.

What is claimed is:

1. A method for predicting a density of micro crystal defects in a production semiconductor element produced from thermal treatment of a production silicon wafer, said method comprising:
    a first step of measuring a test coefficient ratio threshold value for a plurality of test silicon wafers, said first step including,
        forming an infrared absorption spectrum for each of the test silicon wafers prior to thermally treating the respective test silicon wafers to make test semiconductor elements using radiation having a wavenumber range of 1500 to 450 $cm^{-1}$, the spectrum including a first oxygen absorption peak representative of a first oxygen concentration and appearing in the wavenumber range of 1150 to 1050 $cm^{-1}$ and a second oxygen absorption peak representative of a second oxygen concentration and appearing within the wavenumber range of 530 to 500 $cm^{-1}$,
        reading from the spectrum and defining as a first coefficient a magnitude of the first oxygen absorption peak, and reading from the spectrum and defining as a second coefficient a magnitude of the second absorption peak, for each of the test silicon wafers,
        calculating a test coefficient ratio of the first and second coefficients for each of the test silicon wafers,
        thermally treating respective ones of the test silicon wafers to manufacture a plurality of the test semiconductor elements,
        measuring a density of micro crystal defects for each of the test semiconductor elements, and
        selecting as the test coefficient ratio threshold value one of the test coefficient ratios for which the defect density of the test semiconductor elements is a predetermined amount;
    a second step of measuring a production coefficient ratio for the production silicon wafer prior to thermally treating the production silicon wafer to make the production semiconductor element, said second step including,
        forming an infrared absorption spectrum for the production silicon wafer within a wavenumber range of 1500 to 450 $cm^{-1}$, the spectrum including the first oxygen absorption peak and the second oxygen absorption peak,
        reading the first and second coefficients for the production silicon wafer, and
        calculating a production coefficient ratio of the first and second coefficients for the production silicon wafer; and
    a third step of comparing the production coefficient ratio of the production silicon wafer with the test coefficient ratio threshold value to predict a density of the micro crystal defects produced in the production semiconductor element which is to be manufactured from the production silicon wafer.

2. A method according to claim 1, wherein the spectrum forming step of at least one of the first and second steps includes:
    emitting infrared rays;
    superposing the infrared rays onto one another to form an interferogram;
    directing the infrared rays of the interferogram through the silicon wafer;
    detecting the interferogram transmitted through the silicon wafer and converting the interferogram into an electrical signal;
    Fourier-transforming the detected electrical signal to form a spectrum; and
    subtracting from the spectrum a corresponding spectrum of a standard silicon wafer which is free of measurable impurities to obtain an infrared absorption spectrum of the silicon wafer.

3. A method according to claim 1, wherein the reading step of at least one of the first and second steps includes:
    reading a height of the first oxygen absorption peak as the first coefficient; and
    reading a height of the second oxygen absorption peak as the second coefficient.

4. A method according to claim 3, wherein:
    the reading step for at least one of the first and second steps includes reading and defining as a carbon coefficient a magnitude of a carbon absorption peak appearing in the wavenumber range of 615 to 600 $cm^{-1}$ of the infrared absorption spectrum;
    the calculating step for the at least one of the first and the second steps includes calculating a carbon concentration in the silicon wafer from the carbon absorption coefficient; and
    the comparing step includes comparing the carbon concentration with a predetermined carbon concentration value to predict the density of micro crystal defects in the semiconductor element.

5. A method according to claim 1, wherein said test coefficient ratio threshold value is 4.5.

* * * * *